(12) United States Patent
Laughlin (10) Patent No.: US 6,231,550 B1
(45) Date of Patent: May 15, 2001

(54) ONE-HANDED SINGLE GRIP POSITION ASPIRATION AND INJECTION SYRINGE (76) Inventor: Joshua D. Laughlin, 78 Tavern Hill Rd., Putney, VT (US) 05346

( * ) Notice: Subject to any disclaimer, the term of this patent is extended or adjusted under 35 U.S.C. 154(b) by 0 days.

(21) Appl. No.: 09/452,687

(22) Filed: Dec. 2, 1999

(51) Int. Cl.$^7$ .................................................. A61M 5/00
(52) U.S. Cl. ........................................................... 604/187
(58) Field of Search .................................. 604/27, 36, 38, 604/48, 73, 93, 181–182, 187, 218, 227

(56) References Cited

U.S. PATENT DOCUMENTS

| | | |
|---|---|---|
| 1,221,103 | 4/1917 | Sorensen . |
| 3,325,061 | 6/1967 | Ellsworth ............................ 222/386 |
| 3,758,006 | 9/1973 | Gravlee ................................ 222/323 |
| 3,990,446 | 11/1976 | Taylor ................................ 128/218 R |
| 3,993,064 | 11/1976 | McCarthy et al. ................ 128/218 A |
| 4,263,911 | 4/1981 | McCormack et al. ................ 128/276 |
| 4,424,055 | 1/1984 | Herman ................................ 604/36 |
| 4,484,915 | 11/1984 | Tartaglia .............................. 604/227 |
| 4,639,248 | 1/1987 | Schweblin ............................ 604/187 |
| 4,664,128 | 5/1987 | Lee ....................................... 128/753 |
| 5,135,511 | 8/1992 | Houghton et al. ................... 604/220 |
| 5,582,595 | 12/1996 | Haber et al. ......................... 604/187 |
| 5,814,023 | * 9/1998 | Fulk et al. . |
| 5,902,278 | 5/1999 | Aguilar .................................. 604/227 |

* cited by examiner

*Primary Examiner*—Sharon Kennedy
*Assistant Examiner*—Catherine Serke
(74) *Attorney, Agent, or Firm*—Michael J. Weins; Jeffrey S. Sempreban (57) ABSTRACT

An injection and aspiration syringe is designed for operation in either mode with the same finger grip. The syringe has a barrel with wings located at a proximal end region and a central passage, a plunger assembly having a plunger stem terminating in a plunger free end and a plunger head which slidably engages the central passage, and a barrel attachment which engages the barrel and has an associated attachment stem. The barrel attachment can be affixed to the barrel, with the attachment stem slidably engaging the barrel attachment. Alternatively, the barrel attachment can slidably engage the barrel and have the attachment stem affixed thereto. The plunger stem and the attachment stem are interlinked to move in opposition to each other, such that the plunger stem is raised by depressing the attachment stem. A flexible filament attached to the plunger stem, passing along the central passage, over the proximal end region of the barrel, and down the barrel to the attachment stem can be employed to provide a pulley-like action between the plunger stem and the attachment stem. Alternatively, a pinion gear can be mounted in the proximal end region of the barrel to engage racks on the plunger stem and the attachment stem.

16 Claims, 8 Drawing Sheets

ONE-HANDED SINGLE GRIP POSITION ASPIRATION AND INJECTION SYRINGE

FIELD OF THE INVENTION

The present invention relates to a one-handed, finger-gripped, thumb activated syringe that can be used in both injection and aspiration modes, and more particularly one which can be operated in either mode from a single finger gripping position and which is activated in either mode by a single thumb action where the thumb is advanced towards the fingers.

Background of the Invention

There are various one-handed finger-gripped injection and aspiration syringes, which predominantly fall into two types. U.S. Pat. Nos. 3,990,446; 4,639,248; 5,135,511; and 5,582,595 teach one type, where changing the mode of operation requires repositioning the fingers which grip the syringe. This requirement complicates control and operation of the syringe when it is to be used in both modes. The second type, taught in U.S. Pat. Nos. 3,758,006 and 5,902,278, requires pushing and pulling of a plunger stem with the thumb to change modes. The action of pulling using the thumb is contrary to the normal grasping action of the hand, which makes control of the syringe in the aspiration mode difficult. Thus, there is a need for a finger gripped injecting and aspirating syringe where the finger grip remains unchanged as the mode is changed, and where the thumb is advanced towards the fingers in both modes to provide better control of the syringe.

SUMMARY OF THE INVENTION

The present invention is a syringe which can readily be used in an injection mode or an aspiration mode while being held in one hand. The syringe is operated in either mode with a single gripping position of the user's fingers, and in both modes is activated by advancement of the user's thumb toward the fingers which grip the syringe. The invention is particularly well suited for use as a hypodermic syringe, but may also be employed for other types of syringes, such as irrigation syringes and suction syringes. The syringe has a barrel having a central passage and a longitudinal axis. The barrel terminates in a distal end region and a proximal end region, and has a pair of finger-engageable wings attached to the proximal end region of the barrel, which are preferably symmetrically disposed about the barrel. The finger-engageable wings assist the user in stabilizing the barrel in the hand of the user by providing finger grips which are engaged by the fingers with the same gripping action when operating the syringe in both the injection mode and the aspiration mode, thus allowing the user to change modes without altering the finger position.

The syringe has a plunger assembly having a plunger stem. The plunger stem terminates in a plunger head region and a plunger stem free end. The plunger head region has a plunger head configured to slidably and sealably engage the central passage of the barrel. The plunger stem is axially aligned with the longitudinal axis of the barrel and preferably of sufficient length that the plunger stem free end extends beyond the proximal end region of the barrel when the plunger head resides in the distal end region of the barrel. It is also preferred that the plunger stem free end is provided with a plunger thumb pad for the comfort of the user by distributing pressure on the thumb when depressing the plunger stem when operating the syringe in the injection mode.

A barrel attachment is provided, which engages the barrel and has an associated attachment stem. The attachment stem has an attachment stem distal end region and an attachment stem proximal end region terminating in an attachment stem free end. In one preferred embodiment, the barrel attachment is affixed to the barrel and the attachment stem slidably engages the barrel attachment. It is further preferred that one of the wings have an attachment stem passage therethrough, and that the barrel attachment be so positioned that the attachment stem passes through the attachment stem passage.

In other embodiments, the barrel attachment slidably engages the barrel and the attachment stem has the attachment stem distal end region affixed to the barrel attachment or made integral therewith. The attachment stem is preferably of sufficient length that the attachment stem free end extends beyond the proximal end region of the barrel when the barrel attachment resides at the distal end region of the barrel. In one such embodiment, the slidable barrel attachment is a clip which engages the barrel. In another embodiment, a sleeve which encircles the barrel is employed as the slidable barrel attachment.

For all embodiments, it is preferred for the attachment stem free end to be fitted with an attachment stem thumb pad which distributes the pressure on the thumb when depressing the attachment stem. When thumb pads are attached to the plunger stem free end and the attachment stem free end, they should be configured such that, when mounted on their respective stems, they can freely pass by each other as the stems are raised and lowered. It is further preferred that the thumb pads be so positioned that they can be readily independently actuated by the thumb of the user by pivotal action of the thumb relative to the fingers, which remain fixably engaged with respect to the barrel and the wings.

For the convenience and comfort of the user and to further stabilize the syringe during aspiration, it is further preferred that the pivotable action of the thumb move the thumb in the direction of the palm when moving from the injection mode to the aspiration mode.

Means for inducing diametrically opposed movement of the plunger stem and the attachment stem are provided. These means provide a mechanism for raising the plunger stem by depressing the attachment stem, allowing the syringe to operate in the aspiration mode.

A flexible filament terminating in a first filament end and a second filament end offers one preferred means for inducing diametrically opposed movement of the plunger stem with respect to the attachment stem. As used herein, the term "flexible filament" includes monofilaments, stranded filaments, and similar flexible elongated elements. The first filament end is attached to the plunger head region of the plunger stem and affixed with respect to the plunger stem such that it does not interfere with the seal between the central passage and the plunger head. The flexible filament passes along the central passage of the barrel, over the proximal end region, and down the barrel to where the second filament end is affixed with respect to the attachment stem distal end region. The second filament end is either directly connected to the attachment stem distal end region or, when the barrel attachment is a clip or sleeve attached to the attachment stem, the second filament end can be attached to the attachment stem distal end region by attaching to the barrel attachment.

Preferably, the flexible filament is positioned such that it will traverse a path which is substantially parallel to the longitudinal axis of the barrel. It is further preferred that a reference plane containing the longitudinal axis of the central passage of the barrel and the flexible filament intersects the attachment thumb pad and that the flexible filament reside substantially within the footprint of the attachment stem thumb pad.

An alternative to employing a flexible filament as the means for inducing diametrically opposed movement of the plunger stem and the attachment stem is to employ a rack and pinion mechanism to provide such means. In such an embodiment, a pinion gear is mounted in the proximal end region of the barrel so as to rotate about an axis which is perpendicular to a radius of the barrel intersecting the pinion gear. The pinion gear extends into the central passage and extends beyond the barrel. The plunger stem is fitted with a plunger stem rack which engages the pinion gear inside of the central passage, while the attachment stem has an attachment stem rack which engages the pinion gear outside the central passage. In combination, the pinion gear, the plunger stem rack, and the attachment stem rack couple the motion of the two stems to reverse the direction of motion of the plunger stem with respect to the attachment stem when one of the stems is displaced by the user's thumb.

BRIEF DESCRIPTION OF THE FIGURES

FIG. 3 is a view from the plane 3—3 of FIG. 1 showing a hand gripping the syringe, which has an attachment stem thumb pad position in a preferred position for a right-handed user. FIG. 3 illustrates a finger position for operating the syringe in an injection mode.

FIG. 16 is a partial exploded view of a syringe having a barrel and a plunger assembly. FIG. 16 illustrates a plunger head region of a plunger stem, and a first filament end of a flexible filament which provides means for raising the plunger stem when an attachment stem is depressed. The first filament end is configured to slidably engage a cavity in the plunger head region of the plunger stem.

BEST MODE OF CARRYING THE INVENTION INTO PRACTICE

Figure 1:
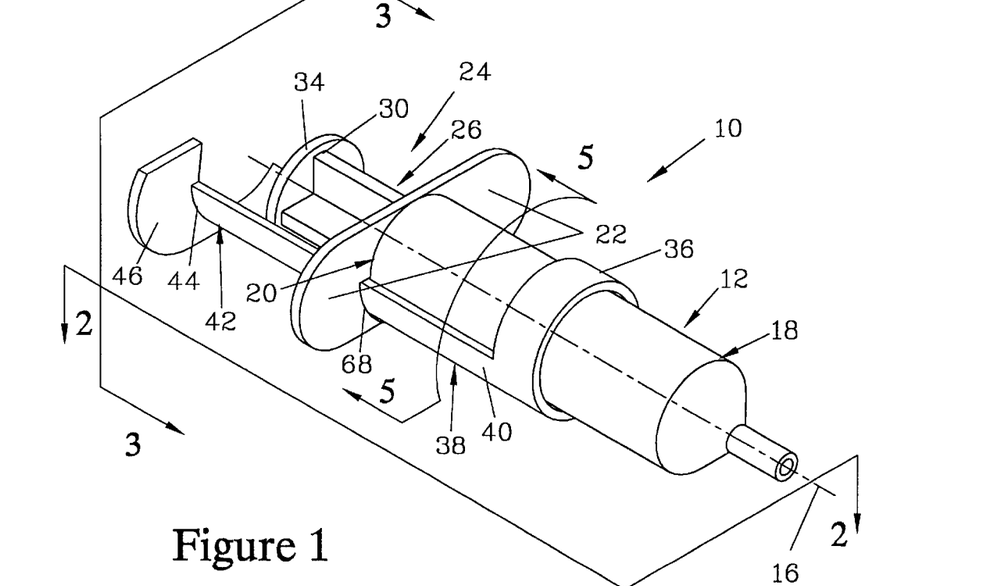
FIG. 1 is an isometric view of a syringe having a barrel, a plunger assembly having a plunger stem, and an attachment stem which is depressed to raise the plunger stem. The syringe employs a sleeve which slidably engages the barrel as well as a flexible filament which serves as means for inducing diametrically opposed movement of a plunger stem and the attachment stem.

FIG. 1 is an isometric illustration of one embodiment of the present invention, a hypodermic syringe 10. The hypodermic syringe 10 is designed to be used in an injection mode, where fluids are injected into a body through a hypodermic needle (not shown), as well as in an aspiration mode, where fluids are withdrawn from the body. The hypodermic syringe 10 is designed for single-handed operation by a user and is manipulated by the user's forefingers and thumb.

The hypodermic syringe 10 has a barrel 12 having a central passage 14 (shown in FIG. 2) with a longitudinal axis 16. The barrel 12 terminates in a distal end region 18 and a proximal end region 20. The barrel 12 has a pair of wings 22 attached to the proximal end region 20 and symmetrically disposed about longitudinal axis 16 of the barrel 12. The wings 22 provide finger grips which assist in stabilizing the barrel 12 in the hand of the user and which remain in contact with the fingers of the user at all times when operating the hypodermic syringe 10, allowing the user to change between the injection mode and the aspiration mode without modifying the user's grip on the barrel 12.

Figure 2:
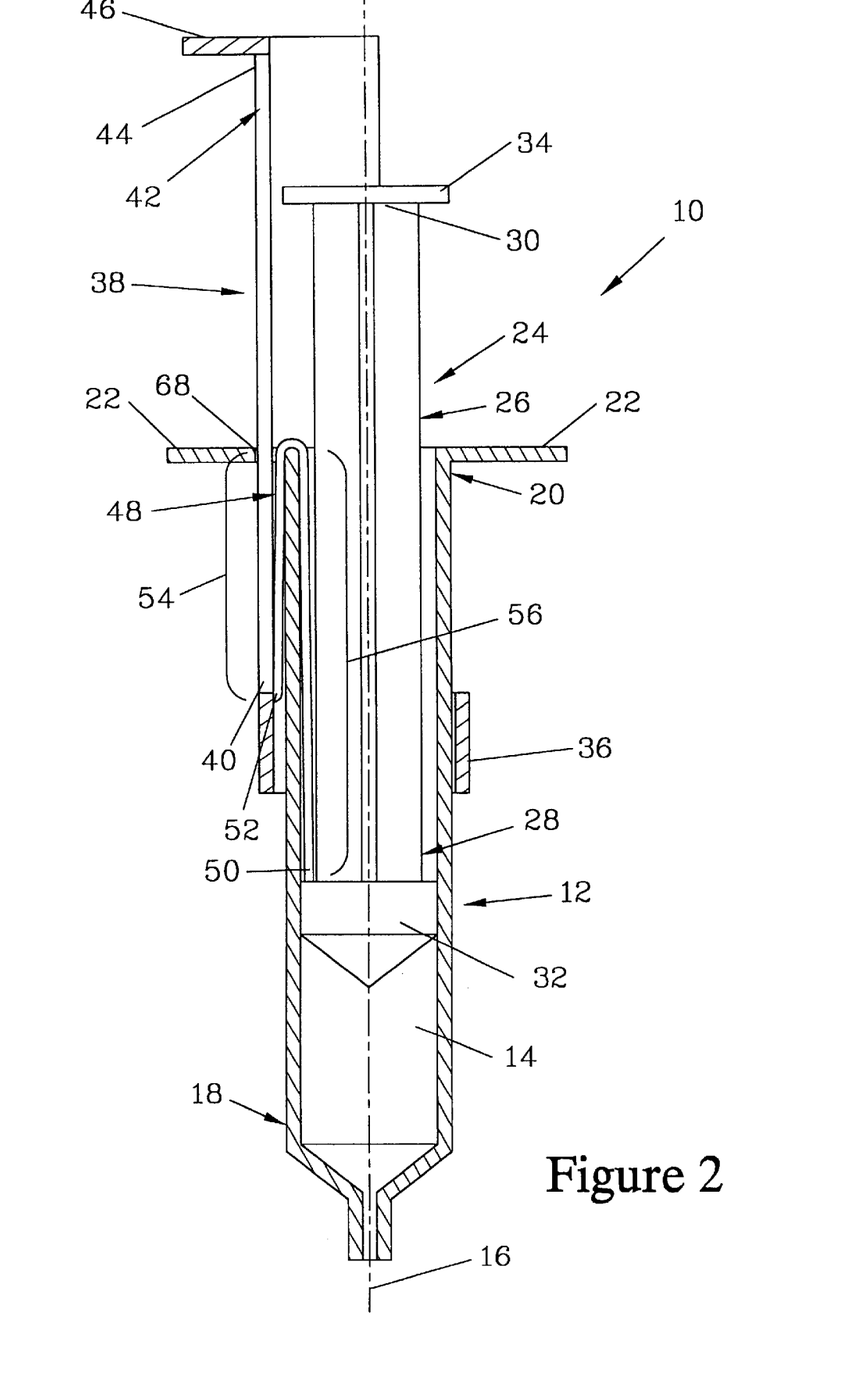
FIG. 2 is a view of section 2—2 of FIG. 1.

FIG. 2 is a view of the section 2—2 of FIG. 1, showing details of a plunger assembly 24. The plunger assembly 24 has a plunger stem 26 terminating in a plunger head region 28 and a plunger stem free end 30. The plunger head region 28 in turn terminates in a plunger head 32 which is configured to slidably and sealably engage the central passage 14 of the barrel 12 of the hypodermic syringe 10. The plunger stem 26 is axially aligned with the longitudinal axis 16 of the barrel 12, and is sufficiently long that the plunger stem free end 30 at all times extends beyond the proximal end region 20 of the barrel 12. The plunger assembly 24 is provided with a plunger thumb pad 34 attached to the plunger stem free end 30 for the comfort of the user. To use the hypodermic syringe 10 in the injection mode, the user depresses the plunger assembly 24 with the user's thumb while gripping the barrel 12 with the index fingers that are engaged with the wings 22.

As best shown in FIG. 1, a sleeve 36 which encircles the barrel 12 serves as a barrel attachment. The sleeve 36 slidably engages the barrel 12 and has an attachment stem 38 connected thereto. The attachment stem 38 has an attachment stem distal end region 40, to which the sleeve 36 is affixed and can be considered to form an integral part thereof. The attachment stem 38 also has an attachment stem proximal end region 42 which terminates in an attachment stem free end 44. The attachment stem free end 44 is fitted with an attachment stem thumb pad 46 for the comfort of the user when depressing the attachment stem 38. The attachment stem thumb pad 46 and the plunger thumb pad 34 are configured such that they are able to pass by each other without interference.

A flexible filament 48, illustrated in FIG. 2, terminates in a first filament end 50 and a second filament end 52. The first filament end 50 is attached to the plunger head region 28 of the plunger assembly 24 in close proximity to the plunger head 32. The flexible filament 48 is strung through the central passage 14 and over the proximal end region 20 of the barrel 12, extending down the barrel 12 to where the second filament end 52 is attached to the attachment stem distal end region 40.

The flexible filament 48 serves as means for inducing diametrically opposed movement of the plunger stem 26 and the attachment stem 38. As the attachment stem 38 is depressed, the sleeve 36 slides toward the distal end region 18 of the barrel 12. This motion extends the length of an outer segment 54 of the flexible filament 48 which resides outside the barrel 12, which in turn reduces the length of an inner segment 56 of the flexible filament 48 which remains in the central passage 14. This reduction in the length of the inner segment 56 of the flexible filament 48 results in plunger head 32 being drawn away from the distal end region 18 of the barrel 12 toward the proximal end region 20. Thus, as the attachment stem 38 is depressed by applying pressure to the attachment stem thumb pad 46, the plunger head 32 is withdrawn from the distal end region 18, placing the hypodermic syringe in the aspiration mode. Conversely, when the plunger stem 26 is depressed by applying pressure on the plunger thumb pad 34, the plunger head 32 is advanced toward the distal end region 18 of the barrel 12, placing the hypodermic syringe 10 in the injection mode. Depressing the plunger stem 26 also causes the sleeve 36 to be moved away from the distal end region 18 of the barrel 12.

Figure 3:
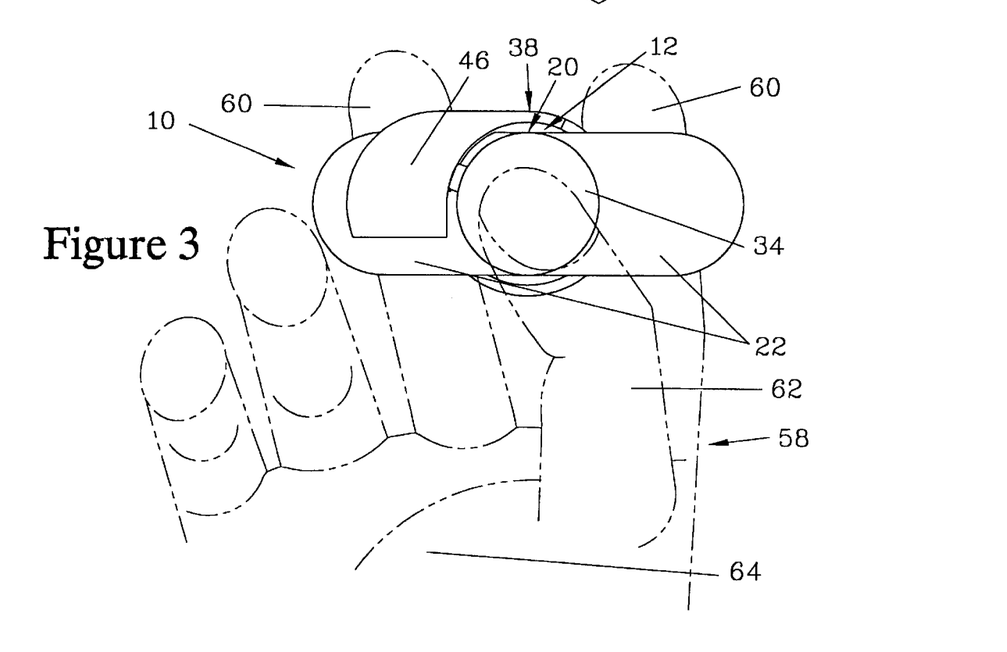
Figure 4:
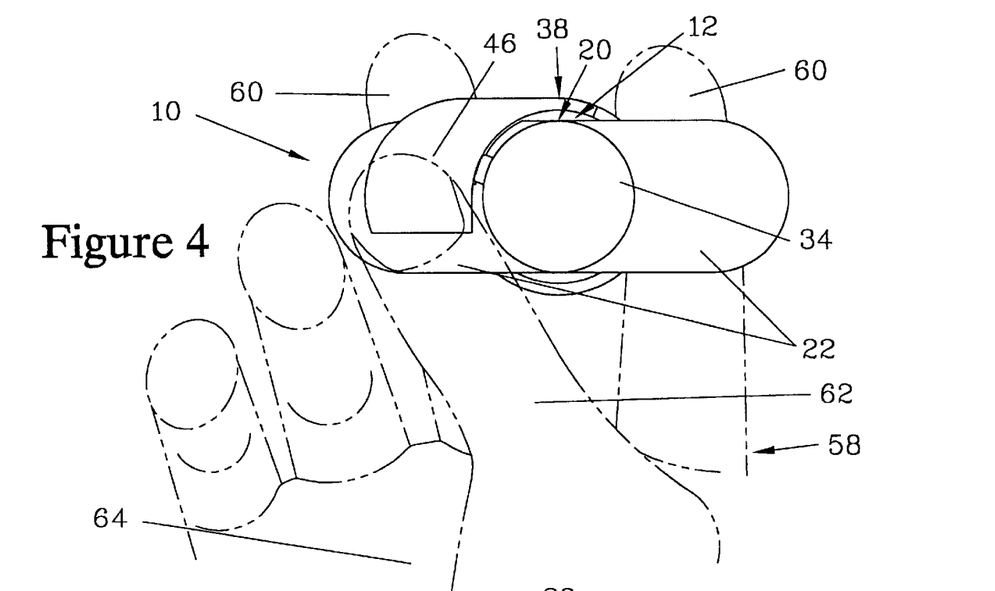
FIG. 4 is a view from the plane 3—3 of FIG. 1, illustrating a finger position for operating the syringe in an aspiration mode.

FIG. 3 shows the hypodermic syringe 10 as viewed from the plane 3—3 of FIG. 1, looking toward the proximal end region 20 of the barrel 12. The hypothermic syringe 10 is designed to be preferably gripped in a user's right hand 58, shown in phantom. The barrel 12 is gripped by the forefingers 60, which are positioned to engage with the wings 22. As illustrated, the thumb 62 of the user is placed on the plunger thumb pad 34, placing the hypodermic syringe 10 in the injection mode. The attachment stem thumb pad 46 is in side-by-side relationship with the plunger thumb pad 34, and is so positioned that it can be independently activated by a pivotal motion of the thumb 62 toward the palm 64 of the hand 58, as illustrated in FIG. 4. Thus, by simple motion of the thumb 62, the user can change the mode of operation from the injection mode to the aspiration mode. Furthermore, changing modes does not require changing the grip on the barrel 12, and both modes are activated by movement of the thumb 62 towards the forefingers 60.

Figure 5:
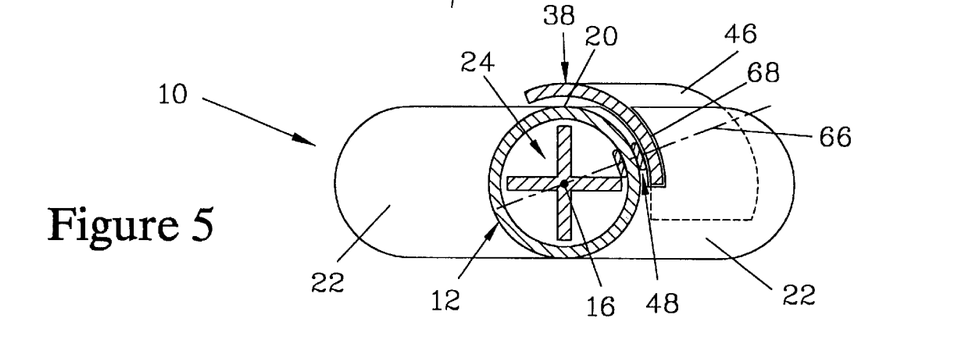
FIG. 5 is a view of section 5—5 of FIG. 1, illustrating the preferred location for the flexible filament with respect to the attachment stem.

FIG. 5 is a view of section 5—5 of FIG. 1, illustrating the spatial relationship of a preferred position for the flexible filament 48 employed in the hypodermic syringe 10. In this embodiment, a flat ribbon is employed as the flexible filament 48. The flexible filament 48 may be constructed of the same material as the plunger assembly 24 and the sleeve 36. These three elements can be fabricated as an integral unit or can be individually made and joined. It is preferred to have the flexible filament 48 traverse a path that is substantially parallel to the longitudinal axis 16 of the barrel 12 to eliminate a torsional component of the force required to raise and lower the plunger head 32 (shown in FIG. 2). It is further preferred that the placement of the attachment stem thumb pad 46 be so positioned that a reference plane 66 which intersects both the longitudinal axis 16 and the flexible filament 48 also intersects the attachment stem thumb pad 46. In order to provide such a position for the stem thumb pad 46, an attachment stem passage 68 is provided in one of the wings 22. A portion of the attachment stem 38 slidably engages the attachment stem passage 68, thereby providing the desired geometric relationship between the attachment stem thumb pad 46 and the flexible filament 48.

Figure 6:
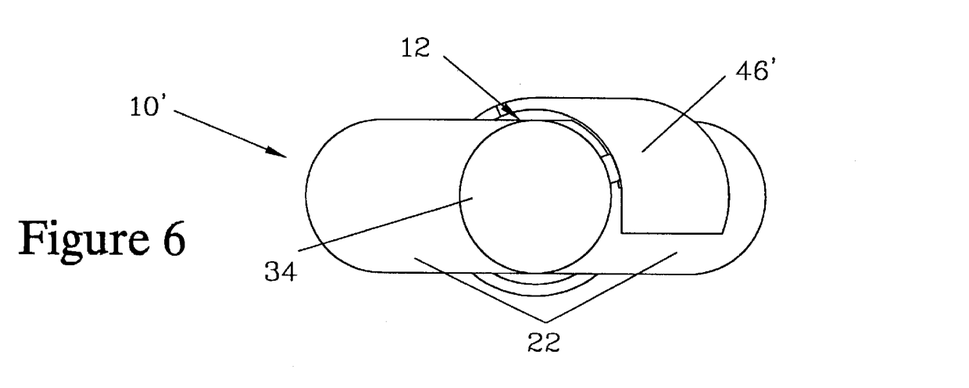
FIG. 6 is an end view of a syringe which forms another embodiment of the present invention, which is similar to the embodiment shown in FIGS. 1–5. This embodiment has an attachment stem thumb pad at an alternate position which is better suited for operation by a left-handed user. The viewing perspective of FIG. 6 corresponds to the viewing perspective of FIGS. 3 and 4.

While the embodiment illustrated in FIGS. 1 through 4 can be used with either the right hand or the left hand, it is less convenient to operate with the left hand. A left-handed hypodermic syringe 10' which can be more conveniently operated with the left hand is illustrated in FIG. 6, which corresponds to the view of FIGS. 3 and 4. The hypodermic syringe 10' is constructed with the attachment stem thumb pad 46' on the opposite side of the hypodermic syringe 10', facilitating use with the left thumb of the user.

Figure 7:
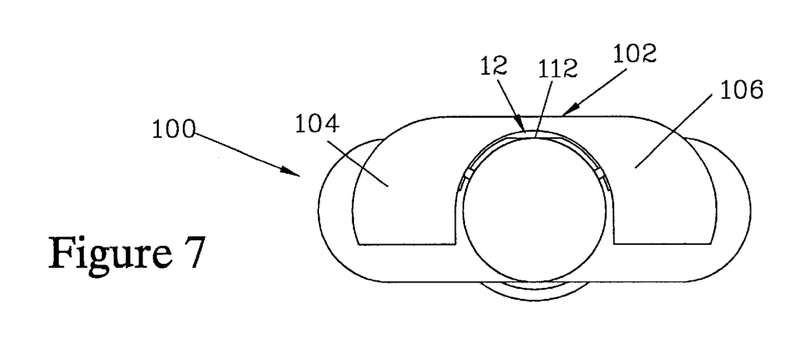
FIG. 7 is a view of another embodiment of the present invention, which is similar to those shown in FIGS. 1–6 but which is designed to be operated by either a left-handed or right-handed user. The viewing perspective of FIG. 7 corresponds to the viewing perspective of FIGS. 3 and 4.
Figure 8:
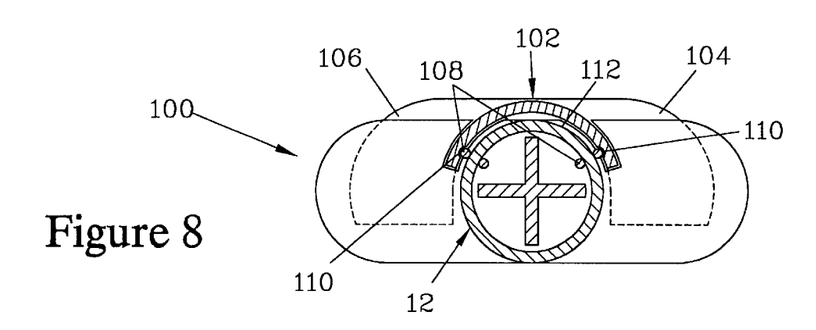
FIG. 8 is a section view of the syringe shown in FIG. 7, and corresponds to the viewing perspective of FIG. 5.

The requirement of having separate left-handed and right-handed hypodermic syringes can be overcome by providing a hypodermic syringe 100 which is designed to be conveniently operated with either hand. The hypodermic syringe 100 illustrated in FIGS. 7 and 8 is well suited for both left-handed operation and right-handed operation. The view of FIG. 7 corresponds to the views of FIGS. 3, 4, and 6, while the view of FIG. 8 corresponds to the view of FIG. 5. The hypodermic syringe 100 has many of the same elements as does the hypodermic syringe 10, and employs the same barrel 12.

The hypodermic syringe 100 differs in that it has an attachment stem 102 which is fitted with both a right-hand attachment stem pad 104 and a left-hand attachment stem pad 106. Each of these thumb pads (104, 106) bears the same geometric relationship to the barrel 12 as the thumb pads (46, 46') described in the embodiments illustrated in FIGS. 3 and 6, which serve to maintain the preferred flexible filament relationship described in the discussion of FIG. 5. However, since there are two thumb pads (104, 106), it is preferred to employ two flexible filaments 108. The flexible filaments 108, which in this embodiment are formed as cords, pass between the barrel 12 and the attachment stem 102 in tracks 110 which are provided in the attachment stem 102. The tracks 110 allow the attachment stem 102 to reside in closer proximity to the barrel 12 of the syringe 100, and add stability to the position of the flexible filaments 108.

For the embodiment shown in FIGS. 7 and 8, the orientation of the syringe 100 makes a side 112 of the barrel 12 readily viewable by the user, independent of the hand in which the syringe 100 is held. Thus, providing indicia on the side 112 allows the indicia to be read by the user when the syringe is used either with the left hand or the right hand.

Figure 9:
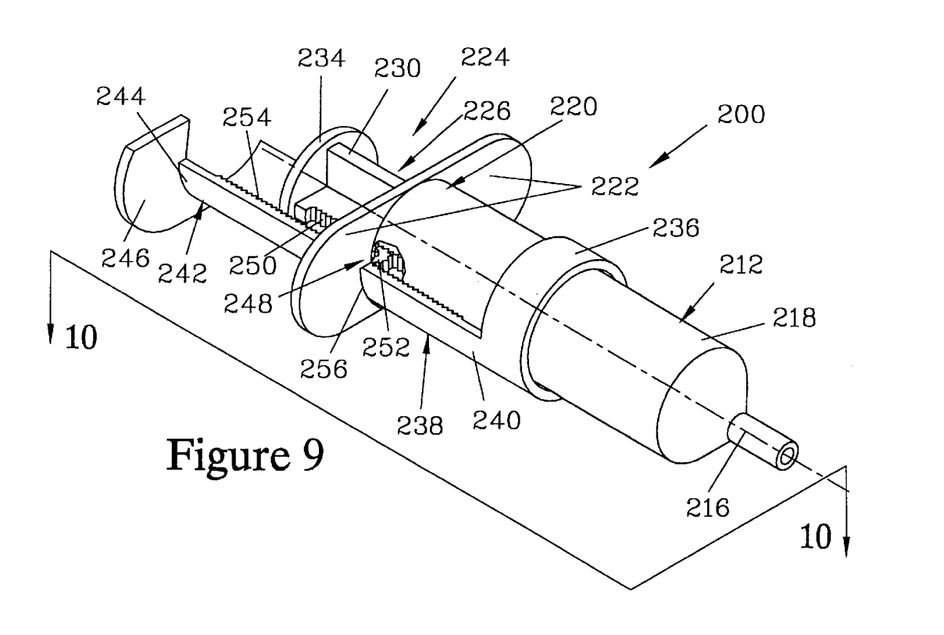
FIG. 9 is an isometric view of a syringe which is similar to that shown in FIGS. 1–5, but differs in that a rack and pinion mechanism provides means for inducing diametrically opposed movement of a plunger stem and an attachment stem.
Figures 10, 11:
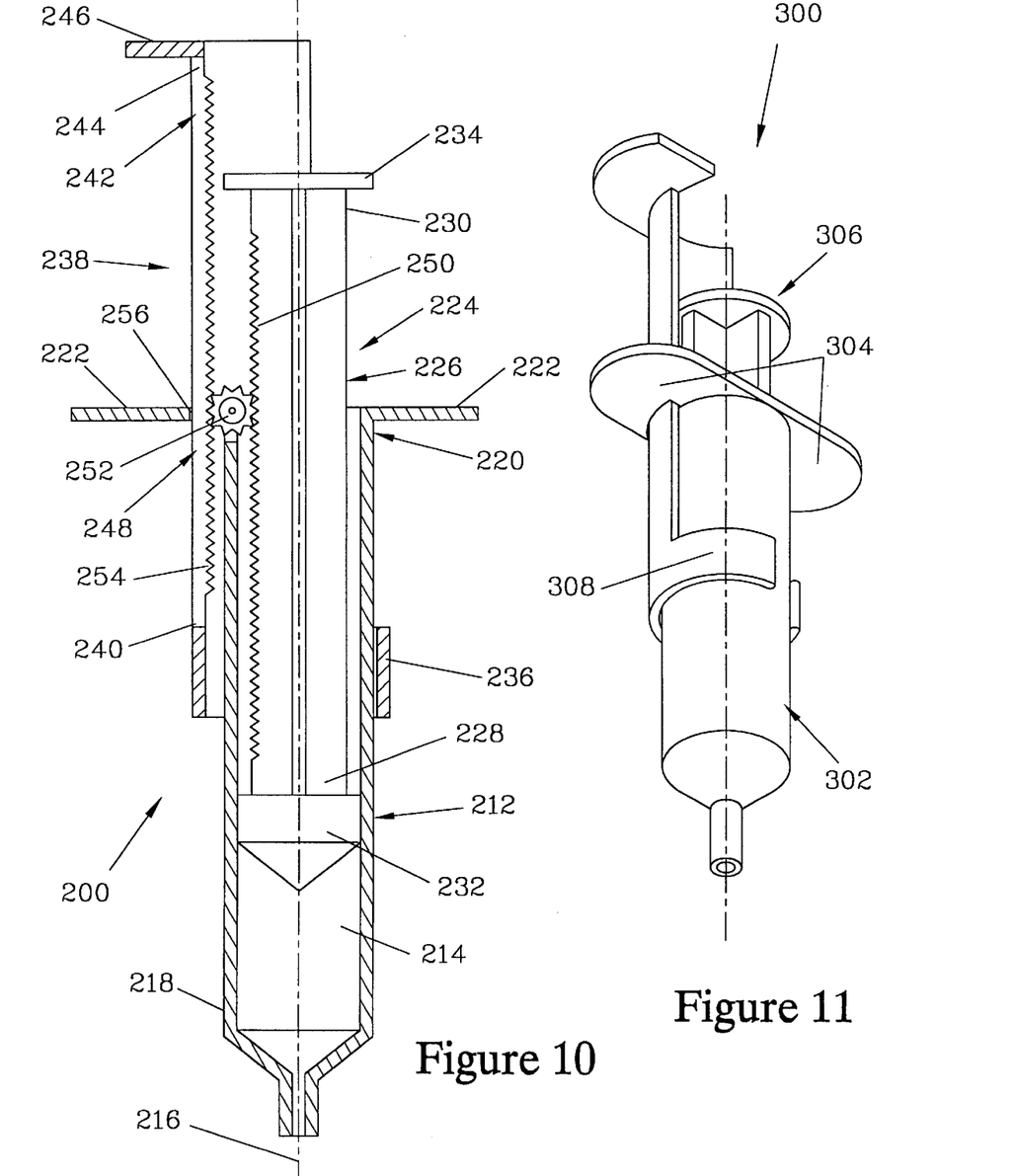
FIG. 10 is a view of the section 10—10 of FIG. 9, showing details of the rack and pinion mechanism.
FIG. 11 is a view of another syringe, which forms another embodiment of the present invention which is similar to that shown in FIGS. 1–5. In this embodiment, the sleeve which slidably engages the barrel of the syringe in the embodiment of FIGS. 1–5 has been replaced with a slidably engaging clip.

FIGS. 9 and 10 illustrate another embodiment of the invention, a hypodermic syringe 200. FIG. 9 is an isometric view of the hypodermic syringe 200, which has a barrel 212 having a central passage 214 (shown in FIG. 10) with a longitudinal axis 216. The barrel 212 terminates in a distal end region 218 and a proximal end region 220. The barrel 212 has a pair of wings 222 attached to the proximal end region 220 and symmetrically disposed about the longitudinal axis 216 to provide finger gripping surfaces.

FIG. 10 is a view of the section 10—10 of FIG. 9 and better illustrates a plunger assembly 224. The plunger assembly 224 has a plunger stem 226. The plunger stem 226 terminates in a plunger head region 228 and in a plunger stem free end 230. The plunger head region 228, in turn, terminates in a plunger head 232. The plunger head 232 is configured to slidably and sealably engage the central passage 214 of the barrel 212. The plunger stem 226 is axially aligned with the longitudinal axis 216 of the barrel 212 and is sufficiently long that the plunger stem free end 230 at all times extends beyond the proximal end region 220 of the barrel 212. The plunger assembly 224 is provided with a plunger thumb pad 234 which is attached to the plunger stem free end 230.

A sleeve 236 (best shown in FIG. 9), which serves as a barrel attachment, slidably engages the barrel 212 of the hypodermic syringe 200. The sleeve 236 has an attachment stem 238 affixed thereto. The attachment stem 238 has an attachment stem distal end region 240, to which the sleeve 236 is affixed, and an attachment stem proximal end region 242 which terminates in an attachment stem free end 244. The attachment stem free end 244 is fitted with an attachment stem thumb pad 246.

The hypodermic syringe 200 differs from the embodiments discussed above in the means which is employed for inducing diametrically opposed movement of the plunger stem 226 and the attachment stem 238. The hypodermic syringe 200 employs a rack and pinion mechanism 248 for inducing such diametrically opposed movement. As best shown in FIG. 10, the hypodermic syringe 200 has a plunger stem rack 250 which is attached to the plunger stem 226 and is positioned to engage a pinion gear 252 rotatably mounted in the proximal end region 220 of the barrel 212. An attachment stem rack 254 is incorporated into the attachment stem 238 and is also positioned to engage the pinion gear 252. Since the plunger stem rack 250 and the attachment stem rack 254 engage opposite sides of the pinion gear 252, they move in opposite directions. Thus, as the attachment stem 238 is depressed and the sleeve 236 slides toward the distal end region 218 of the barrel 212, the pinion gear 252 rotates counterclockwise. This rotation raises the plunger stem rack 250 and the plunger stem 226, resulting in the plunger head 232 being drawn away from the distal end region 218 of the barrel 212 and toward the proximal end region 220. Thus, as the attachment stem 238 is depressed by applying pressure on the attachment stem thumb pad 246, the plunger head 232 is withdrawn from the distal end region 218, placing the hypodermic syringe 200 in the aspiration mode. Conversely, when the plunger stem 226 is depressed by applying pressure on the plunger thumb pad 234, the plunger head 232 is advanced toward the distal end region 218 of the barrel 212, placing the hypodermic syringe 200 in the injection mode. This motion also causes the pinion gear 252 to rotate clockwise, raising the attachment stem rack 254 to move the sleeve 236 away from the distal end region 218 of the barrel 212.

In this embodiment, the attachment stem thumb pad 246 is aligned directly above one of the wings 222, and an attachment stem passage 256 is provided through the wing 222. The attachment stem 238 slidably engages the attachment stem passage 256 to accommodate the alignment of the attachment stem thumb pad 246 and the wing 222.

FIG. 11 illustrates another embodiment of the present invention, a hypodermic syringe 300 which has a barrel 302 with wings 304 and a plunger assembly 306 which are functionally the same as those employed in the earlier embodiments illustrated in FIGS. 1–5 and FIGS. 10 and 11, and either a flexible filament or a rack and pinion mechanism as means for introducing diametrically opposed movement of the plunger stem and the attachment stem.

Again, the hypodermic syringe 300 employs a barrel attachment 308 which is slidably engaged with the barrel 302 of the syringe 300. In this embodiment the barrel attachment 308 is formed as a clip, rather than as a sleeve as in the embodiments discussed above.

FIGS. 12 through 15 illustrate another embodiment of the present invention, a hypodermic syringe 400. The hypodermic syringe 400 has a barrel 412 having a central passage 414 (best illustrated in FIG. 13 which is a section 13—13 of FIG. 12). The central passage in turn has a longitudinal axis 416. The barrel 412 terminates in a distal end region 418 and a proximal end region 420. The barrel 412 has a pair of wings 422 attached to the proximal end region 420 of the barrel 412 and symmetrically disposed about its longitudinal axis 416.

Figures 13, 14:
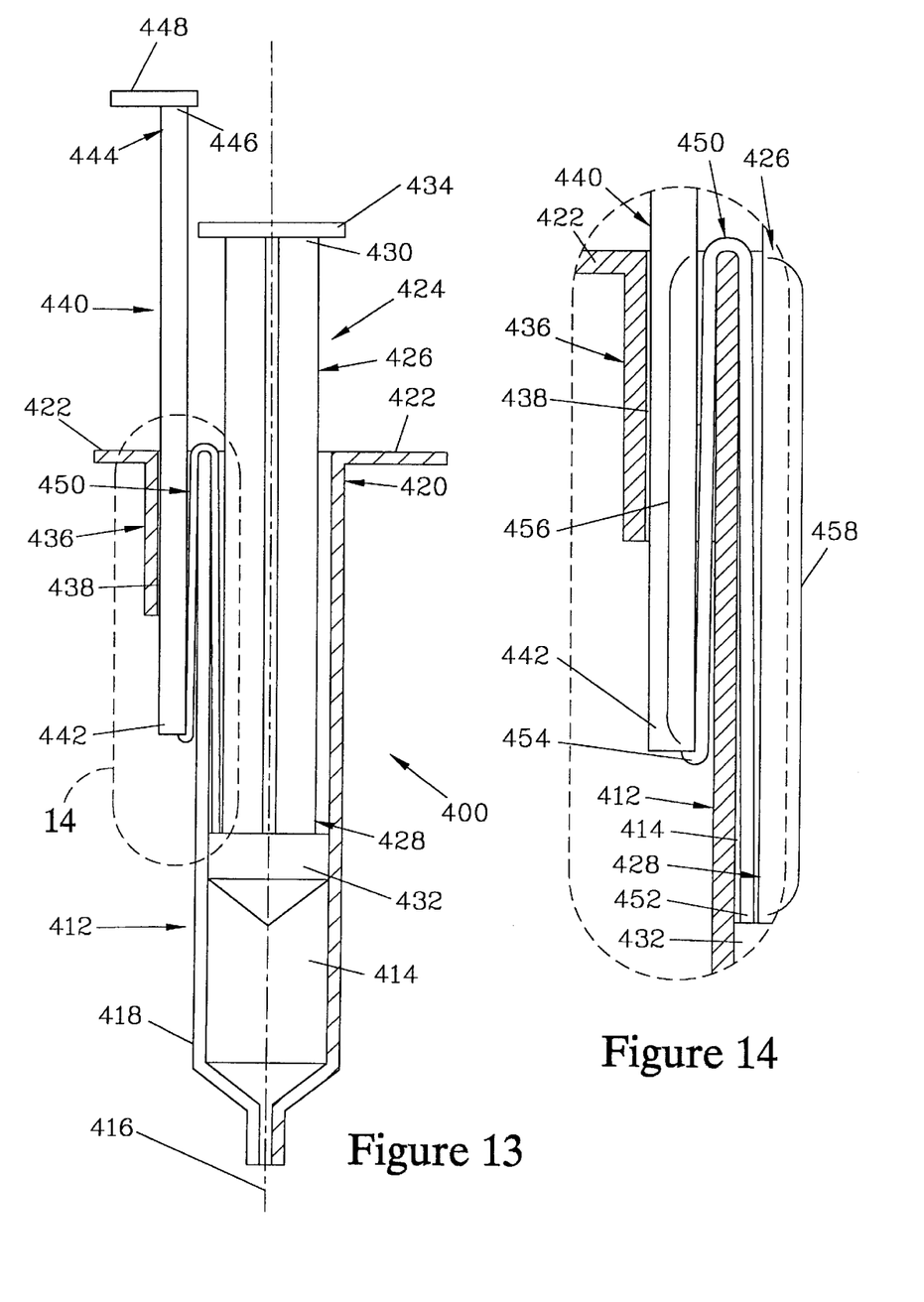
FIG. 13 is a view of the section 13—13 of FIG. 12.
FIG. 14 is a view of the region 14 of FIG. 13.

FIG. 13 shows details of a plunger assembly 424 employed in the syringe 400. The plunger assembly 424 has a plunger stem 426 which terminates in a plunger head region 428 and a plunger free end 430. The plunger head region 428 in turn has a plunger head 432 which is configured to slidably and sealably engage the central passage 414 of the barrel 412. The plunger assembly 424 is provided with a plunger thumb pad 434 attached to the plunger free end 430.

Referring again to FIG. 12, a barrel attachment 436 is affixed to the barrel 412 of the hypodermic syringe 400 and can be formed as an integral part thereof. In the syringe 400, the barrel attachment 436 is also an integral part of one of the wings 422 as is best seen in FIG. 14 which is an enlargement of the region 14 of FIG. 13. The barrel attachment 436 is formed with an attachment passage 438 extending through both the barrel attachment 436 and the wing 422 which is integral with the barrel attachment 436.

Figure 12:
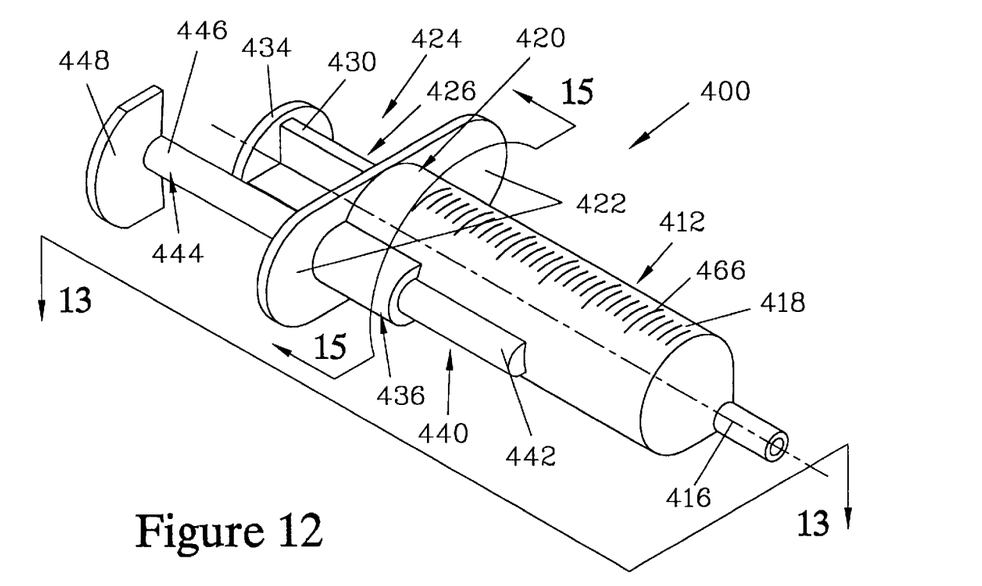
FIG. 12 is an isometric view of a syringe which forms another embodiment of the present invention, which differs in that it employs a barrel attachment which is affixed to the barrel, and which is slidably engaged by the attachment stem.

An attachment stem 440 is provided which has an attachment stem distal end region 442 and an attachment stem proximal end region 444 terminating in an attachment stem free end 446. The attachment stem 440 passes through the attachment passage 438 to provide a slidable engagement of the attachment stem 440 with the barrel attachment 436. The attachment stem 440 is positioned in the attachment passage 438 such that the attachment stem free end 446 extends beyond the wing 422, and the attachment stem free end 446 is fitted with an attachment stem thumb pad 448 which prevents passage of the attachment stem 440 through the attachment passage 438. The attachment stem thumb pad 448 is configured such that it can pass by the plunger thumb pad 434 without interference.

While a rack and pinion mechanism such as that shown in FIGS. 9 and 10 could be employed as means for inducing diametrically opposed movement of the plunger stem 426 and the attachment stem 440, the hypodermic syringe 400 employs a flexible filament 450 to provide such means. As best illustrated in FIG. 14, the flexible filament 450 terminates in a first filament end 452 and a second filament end 454. The first filament end 452 is attached to the plunger head region 428 in close proximity to the plunger head 432. The flexible filament 450 extends through the central passage 414 and over the proximal end region 420 of the barrel 412, passing through the attachment passage 438 and extending down the barrel 412. The second filament end 454 is attached to the attachment stem distal end region 442 of the attachment stem 440.

As the attachment stem 440 is depressed, the attachment stem distal end region 442 slides toward the distal end region 418 of the barrel 412. This motion extends an outer segment 456 of the flexible filament 450 which resides outside the barrel 412, which in turn reduces an inner segment 458 of the flexible filament 450 which remains in the central passage 414. This reduction in the inner segment 458 of the flexible filament 450 results in the plunger head 432 being drawn away from the distal end region 418 of the barrel 412 toward the proximal end region 420. Thus, as the attachment stem 440 is depressed by applying pressure on the attachment stem thumb pad 448, the plunger head 432 is withdrawn from the distal end region 418, placing the hypodermic syringe 400 in the aspiration mode. Conversely, when the plunger stem 426 is depressed by applying pressure on the plunger thumb pad 434, the plunger head 432 is advanced toward the distal end region 418 of the barrel 412, placing the hypodermic syringe 400 in the injection mode. Depressing the plunger stem 426 also causes the attachment stem distal end region 442 to be moved away from the distal end region 418 of the barrel 412.

Figure 15:
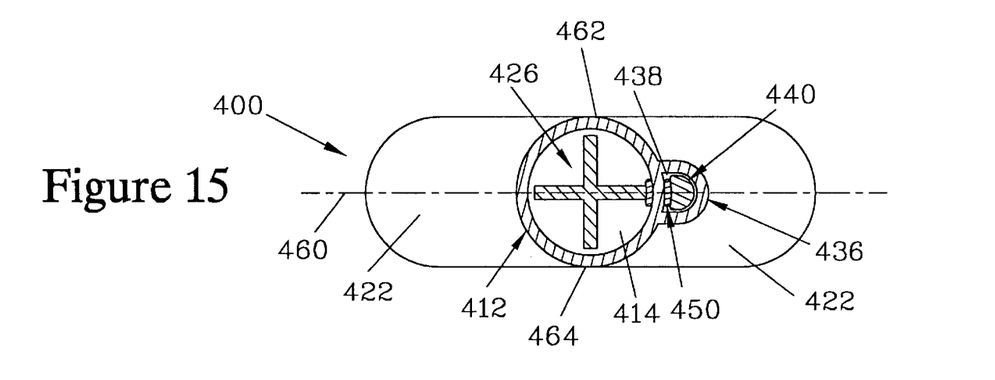
FIG. 15 is a view of the section 15—15 of FIG. 12.

FIG. 15 illustrates the section 15—15 of FIG. 12 and shows the symmetry of the resulting syringe 400 about a plane 460, which divides the barrel 412 into a first region 462 and a second region 464. This symmetry makes the syringe 400 equally convenient for both right-handed and left-handed use. However, since the syringe 400 is oriented differently for right-handed and left-handed use, it is preferred for indicia 466 to be provided both on the first region 462 (as shown in FIG. 12) and on the second region 464 of the barrel 412.

Figure 16:
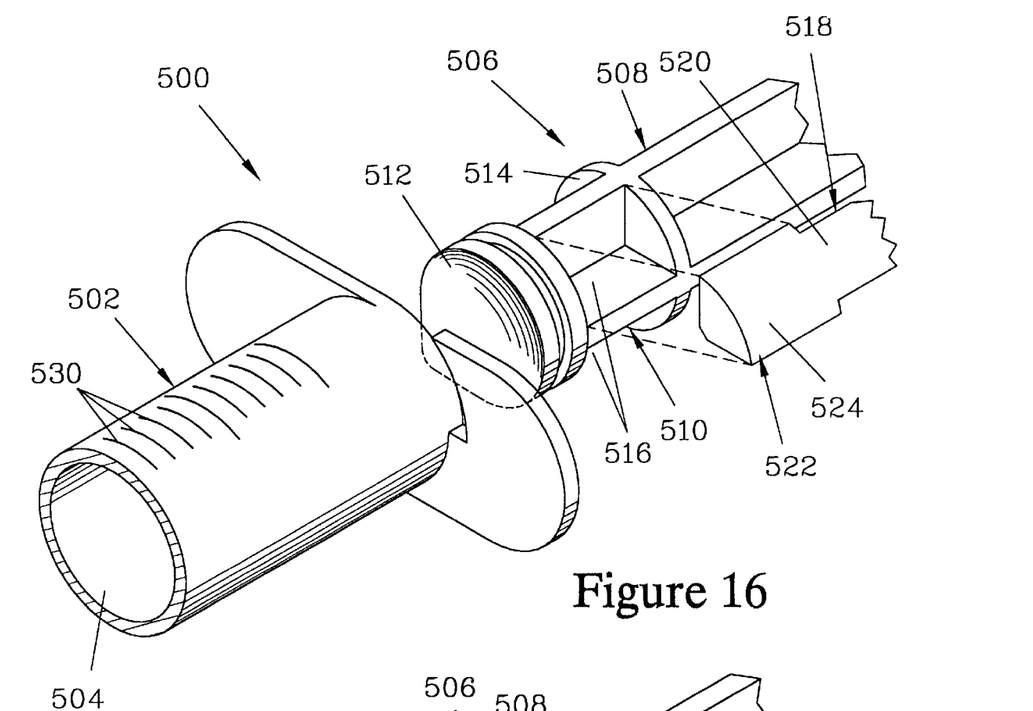
Figure 17:
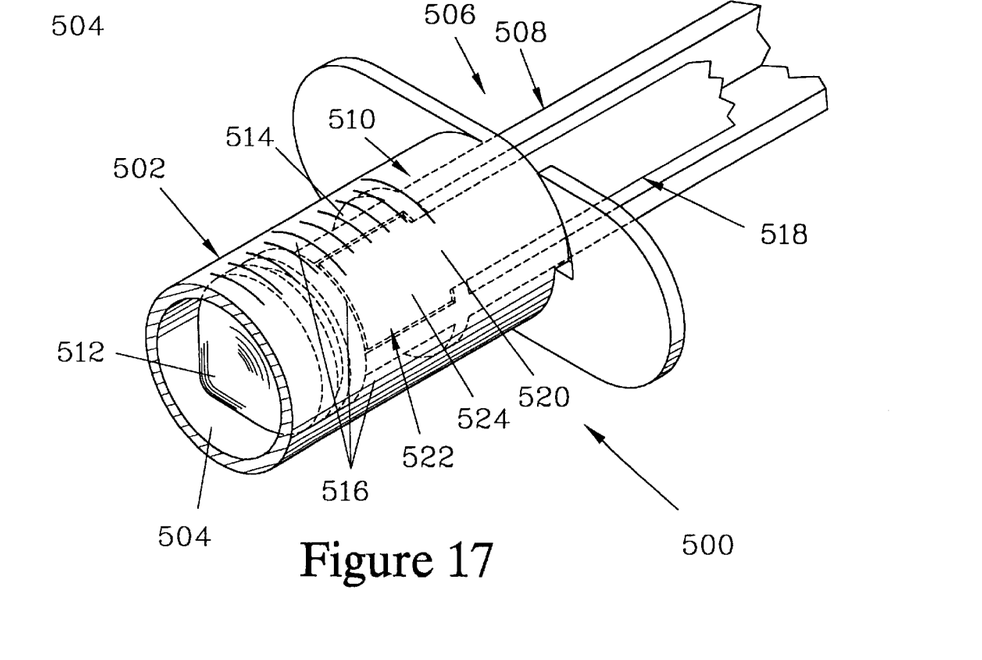
FIG. 17 is an isometric view which shows the barrel, plunger assembly, and flexible filament of FIG. 16 assembled.

FIGS. 16 and 17 illustrate part of a hypodermic syringe 500, which again has a barrel 502 having a central passage 504. A plunger assembly 506 is provided, having a cruciform plunger stem 508. The cruciform plunger stem 508 terminates in a plunger head region 510 which again has a plunger head 512 configured to slidably and sealably engage the central passage 504. In this embodiment, the plunger head region 510 also has a rib member 514, which is spaced apart from the plunger head 512 so as to define four wedge-shaped cavities 516.

A flexible filament 518 serves as means for inducing diametrically opposed movement of the plunger stem 508 and an attachment stem (not shown). The flexible filament 518 terminates in a first filament end 520. In this embodiment, the first filament end 520 is attached to a chock 522 which can be made an integral part of the first filament end 520. The chock 522 is configured to seat in one of the wedge-shaped cavities 516. The attachment of the first filament end 520 is preferably located on an outer edge 524 of the chock 522, allowing the flexible filament 518 to pass over the rib member 514. To attach the first filament end 520 to the plunger head region 510, the chock 522 is inserted into one of the wedge-shaped cavities 516 and the plunger head region 510 is inserted into the central passage 504 of the barrel 502, as shown in FIG. 17. The central passage 504 confines the chock 522 and maintains it within the wedge-shaped cavity 516, while the flexible filament 518 passes between the rib member 514 and the central passage 504. The engagement of the chock 522 with the wedge-shaped cavity 516 serves to attach the first filament end 520 to the plunger head region 510 in close proximity to the plunger head 512.

The embodiment of FIGS. 16 and 17 is well suited to be incorporated with the embodiments shown in FIGS. 1–8.

FIGS. 16 and 17 also show a set of indicia 530 which can be provided on the barrel 512 to indicate the current volume of the barrel 512.

While the novel features of the present invention have been described in terms of particular embodiments and preferred applications, it should be appreciated by one skilled in the art that substitution of materials and modification of details obviously can be made without departing from the spirit of the invention.

What I claim is:

1. A syringe which facilitates one handed operation for both injection and aspiration without modification of a user's grip on the syringe by the user's fingers and which accomplishes both injection and aspiration by movement of the user's thumb towards the user's fingers, the syringe comprising:

a barrel having a central passage with a longitudinal axis and terminating in a distal end region and a proximal end region;

a pair of finger-engageable wings attached to said proximal end region;

a plunger assembly having a plunger stem terminating in a plunger head region and a plunger stem free end, said plunger head region in turn having a plunger head configured to slidably and sealably engage said central passage of said barrel;

a barrel attachment engaging the barrel, said barrel attachment having an attachment stem associated therewith which has an attachment stem distal end region and an attachment stem proximal end region terminating in an attachment stem free end, said attachment stem being movable with respect to said barrel; and means for inducing diametrically opposed movement of said plunger stem and said attachment stem with respect to said barrel.

2. The syringe of claim 1 wherein said means for inducing diametrically opposed movement of said plunger stem and said attachment stem further comprises:

a flexible filament terminating in a first filament end and a second filament end, said first filament end attaching to said plunger head region and said second filament end attaching to said attachment stem distal end region, said flexible filament passing over said proximal end region of said barrel.

3. The syringe of claim 2 further comprising:

a plunger stem thumb pad attached to said plunger stem free end; and an attachment stem thumb pad attached to said attachment stem free end, said plunger stem thumb pad and said attachment stem thumb pad being so positioned and configured that said plunger stem thumb pad does not project onto said attachment stem thumb pad when viewed along said longitudinal axis of said barrel, and said plunger stem thumb pad and said attachment stem thumb pad have at least in part a side-by-side relationship such that said attachment stem thumb pad, in part, projects onto at least part of one of said pair of finger-engageable wings.

4. The syringe of claim 2 wherein said barrel attachment is affixed to said barrel and said attachment stem slidably engages said barrel attachment.

5. The syringe of claim 2 wherein said barrel attachment is slidably engaged with said barrel and said attachment stem is affixed with respect to said barrel attachment.

6. The syringe of claim 5 wherein said barrel attachment is a clip.

7. The syringe of claim 6 wherein said second filament end attaches to said attachment stem distal end region by attaching to said clip.

8. The syringe of claim 5 wherein said barrel attachment is a sleeve which encircles said barrel.

9. The syringe of claim 8 wherein said second filament end attaches to said attachment stem distal end region by attaching to said sleeve.

10. The syringe of claim 1 wherein said means for inducing diametrically opposed movement of said plunger stem and said attachment stem further comprises:
   a plunger stem rack attached to said plunger stem;
   an attachment stem rack attached to said attachment stem; and
   a pinion gear rotatably mounted to said proximal end region of said barrel and engaged with said plunger stem rack and said attachment stem rack.

11. The syringe of claim 10 further comprising:
   a plunger stem thumb pad attached to said plunger stem free end; and
   an attachment stem thumb pad attached to said attachment stem free end,
      said plunger stem thumb pad and said attachment stem thumb pad being so positioned and configured that said plunger stem thumb pad does not project onto said attachment stem thumb pad when viewed along said longitudinal axis of said barrel, and said plunger stem thumb pad and said attachment stem thumb pad have at least in part a side-by-side relationship such that said attachment stem thumb pad, in part, projects onto at least part of one of said pair of finger-engageable wings.

12. The syringe of claim 10 wherein said barrel attachment is affixed to said barrel and said attachment stem slidably engages said barrel attachment.

13. The syringe of claim 10 wherein said barrel attachment is slidably engaged with said barrel and said attachment stem is affixed to said barrel attachment.

14. The syringe of claim 13 wherein said barrel attachment is a clip.

15. The syringe of claim 13 wherein said barrel attachment is a sleeve which encircles said barrel.

16. The syringe of claim 2 wherein said plunger assembly further comprises:
   at least one cavity located in said plunger head region; and
   further wherein said flexible filament further comprises:
      a chock configured to seat in said at least one cavity and be confined therein when said plunger head region resides in said central passage of said barrel, said chock being attached to said first filament end.

* * * * *